United States Patent [19]

Kim

[11] Patent Number: 5,468,454

[45] Date of Patent: Nov. 21, 1995

[54] COMPACT STERILIZING DEODORIZING AND FRESHNESS-PRESERVING APPARATUS FOR USE IN A REFRIGERATOR

[75] Inventor: Chun T. Kim, Suwon, Rep. of Korea

[73] Assignee: Samsung Electronics Co., Ltd., Suwon, Rep. of Korea

[21] Appl. No.: 223,678

[22] Filed: Apr. 6, 1994

[51] Int. Cl.⁶ ........................................ A61L 9/22
[52] U.S. Cl. .................... 422/121; 422/120; 422/122; 422/186.04
[58] Field of Search ................ 422/1, 4, 5, 22, 422/30, 120, 121, 122, 186.04, 186.05; 250/455.11

[56] References Cited

U.S. PATENT DOCUMENTS

| | | | |
|---|---|---|---|
| 4,244,712 | 1/1981 | Tongret | 422/121 X |
| 4,780,277 | 10/1988 | Tanaka et al. | 422/4 |
| 5,015,442 | 5/1991 | Hirai | 422/121 |
| 5,136,461 | 8/1992 | Zellweger | 422/121 X |
| 5,173,268 | 12/1992 | Weaver | 422/121 X |
| 5,230,220 | 7/1993 | Kang et al. | 422/121 X |

FOREIGN PATENT DOCUMENTS 3-72289  7/1991  Japan .

*Primary Examiner*—Robert J. Warden
*Assistant Examiner*—Krisanne M. Thornton
*Attorney, Agent, or Firm*—Burns, Doane, Swecker & Mathis

[57] ABSTRACT

A multi-function apparatus for use in a refrigerator generates a plurality of positive or negative D.C. voltages to a pointed electrode structure and a strip shaped electrode structure in order to generate corona discharge, thereby sterilizing/deodorizing air in the refrigerator's compartments, and furthermore a separate positive or negative voltage is applied to an ionizing electrode to generate positive or negative ions in the air, thus preserving the freshness of stored foodstuffs for an extended period of time.

4 Claims, 3 Drawing Sheets

COMPACT STERILIZING DEODORIZING AND FRESHNESS-PRESERVING APPARATUS FOR USE IN A REFRIGERATOR

BACKGROUND OF THE INVENTION

The present invention is related to providing a sterilizing/deodorizing apparatus for use in a refrigerator, and in particular to providing a multi-function apparatus for use in a refrigerator which generates positive or negative ions in addition to ozone so that, in addition to sterilizing and deodorizing air in the refrigerator, the multi-function apparatus of the present invention preserves the freshness of stored foodstuffs for an extended period of time. The present invention also relates to providing a multi-function apparatus as described above which takes up no more space than does a conventional apparatus that performs only the sterilizing and deodorizing functions.

PRIOR ART

In general, a refrigerator is used for storing various foodstuffs in either a refrigerated or frozen state in order to maintain the freshness of the foodstuffs long period. Of the refrigerator has a refrigerating cycle including a compressor, an evaporator, a capillary tube, and a condenser. The evaporator, also known as a heat exchanger, is mounted in the an air-flow passage separated from the foodstuff storage spaces. The cooled air is circulated by a blower fan into the foodstuff storage spaces where the foodstuffs are stored in a refrigerated or frozen state.

For example, as shown in FIG. 1, refrigerator 10 is a two door type unit divided into a freezing compartment 1 and a refrigerating compartment 2, which has a refrigerating cycle (not shown) including a compressor and a condenser, properly mounted in the rear lower portion and an evaporator installed between the partition walls of the freezing compartment 1 and the refrigerating compartment 2. Thus, air taken from outside the unit is cooled and introduced through a cool air supply portion 4 into the refrigerating compartment 2. In the refrigerating compartment 2, the cool air supply portion 4 is mounted in the center of the upper rear wall and a freezer drawer compartment 3 is installed adjacent to the cool air supply portion 4 for the selective storage of foodstuffs.

Preservation of freshness of foodstuffs for an extended period of time is an important goal for the refrigerating unit 10. The modern approach is to keep the temperature of the freezing and refrigerating compartments constant. But, it is not possible to store foodstuffs at a constant optimum temperature because of the opening and closing of the refrigerator access doors. Even if the storage compartments could maintain uniform temperatures, the stored foodstuffs would have limited shelf-lives due to the presence of bacteria in the foodstuffs and due to odors and aerobic bacteria in the air in the refrigerator.

In order to resolve these problems, a sterilizing/deodorizing apparatus 5 is installed adjacent to the cooling air supply portion 4 in the refrigerator 10. The sterilizing/deodorizing apparatus 5 as described in the prior art is provided with an ozone generator. Conventional sterilizing/deodorizing apparatus are divided into two types: ultraviolet ray lamps and ozone generators. The conventional sterilizing/deodorizing apparatus functions to sterilize floating bacteria and to remove odors, but does not arrest the activity of bacteria in the foodstuffs themselves, and thus does not preserve freshness for an extended period of time.

A typical sterilizing/deodorizing apparatus as shown in FIG. 2 is disclosed in Japan Laid-Open Utility Model Publication No. 91-72289. The sterilizing/deodorizing apparatus includes a housing 151 in which a high voltage generator 152, a first electrode 152a, a second electrode 152b, and a deodorizing catalyzer layer 153 are arranged, respectively, in sequence from an air inlet portion to an air outlet portion.

During its operation, the high voltage generator 152 applies a high voltage current to the electrodes 152a and 152b in order to cause a corona discharge which generates ozone $O_3$, thereby sterilizing any bacteria floating in the air and removing odors from the air. Next, the ozone-containing air passes through a catalyzer layer 153 to be neutralized. Thus, the sterilizing/deodorizing apparatus has a disadvantage in that bacteria contained in the foodstuffs are not completely removed. The sterilizing/deodorizing apparatus only enables foodstuffs to be stored in a clean environment, but does not function to preserve the freshness for an extended period of time.

It is known that generating positive or negative ions in the refrigerator causes the activity of bacteria in the foodstuffs to be rested or respited, thereby restraining the phenomena of aging. This is a known method of keeping foodstuffs fresh.

But, the installation of an ion generating apparatus in the refrigerator typically causes the manufacturing costs to be increased and reduces the overall foodstuff storage space.

Thus, the main object of the invention is to provide a multi-function apparatus for the use in a refrigerator for sterilizing/deodorizing foodstuffs and for preserving the freshness thereof without consuming additional space in the storage compartments.

The other object of the invention is to provide a multi-function additional apparatus for the use of a refrigerator for generating positive or negative ions and for providing a sterilizing/deodorizing process.

Another object of the invention is to provide a multi-function apparatus for use in a refrigerator whereby a sterilizing/deodorizing function and a freshness preserving function is executed by a high voltage generator.

The invention provides a multi-function apparatus for use in a refrigerator which comprises a housing forming an air inlet portion and an air outlet portion at the upper and lower portion of the apparatus; a power source portion mounted in the housing and including a high voltage generator for generating a plurality of positive or negative high voltages and a printed circuit board for controlling the operation of the system, provided with an indication light which enables users to monitor the system operation and an on/off switch for controlling the power source; and a multi-function additional portion including an ozone generating portion, provided with a pointed electrode structure and a strip shaped electrode structure arranged in sequence at predetermined intervals from the air inlet portion to provide the corona discharge, an ozone resolving portion for preventing ozone from passing through the ozone generating portion and an ionizing electrode portion, in the form of a single pointed electrode for generating positive or negative ions during the application of high voltage.

It is noted in the invention that only one high voltage generating portion applies at least two high voltages to the ozone generating portion and selectively to the ionizing electrode portion. The ozone generating portion functions to sterilize/deodorize air introduced therein, the ozone resolving portion reduces the ozone to discharge clean air, and the ionizing electrode portion forces the clean air to have positive or negative ions so that the activity of bacteria in the stored foodstuffs is rested and the freshness of the foodstuffs is preserved for an extended period of time.

BRIEF DESCRIPTION OF THE DRAWINGS

The invention will now be described in detail with reference to the attached drawings, in which.

DETAILED DESCRIPTION OF THE INVENTION

Figure 1:
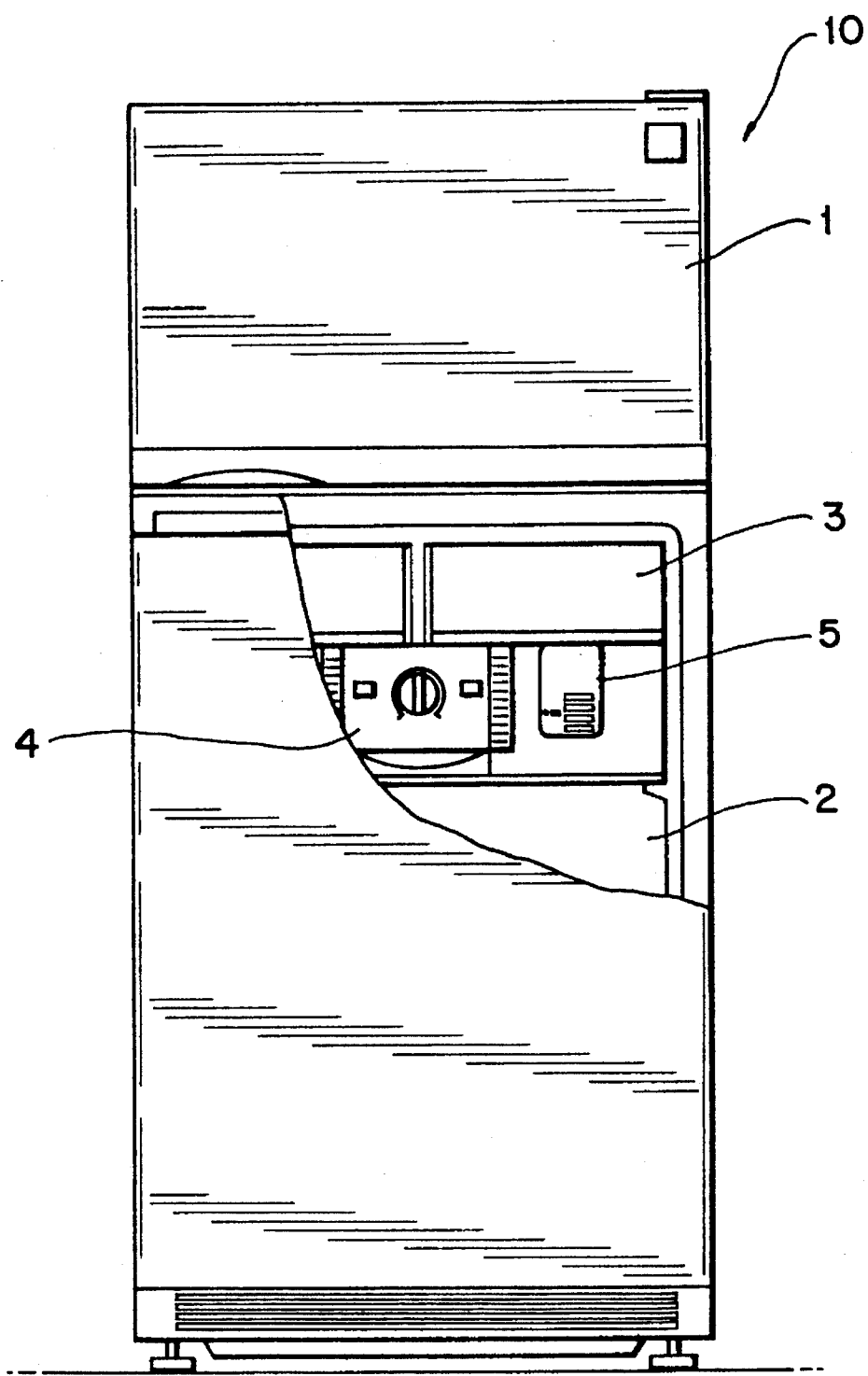
FIG. 1 is a view illustrating a general refrigerator cut open in part, to which the invention is adapted.
Figure 2:
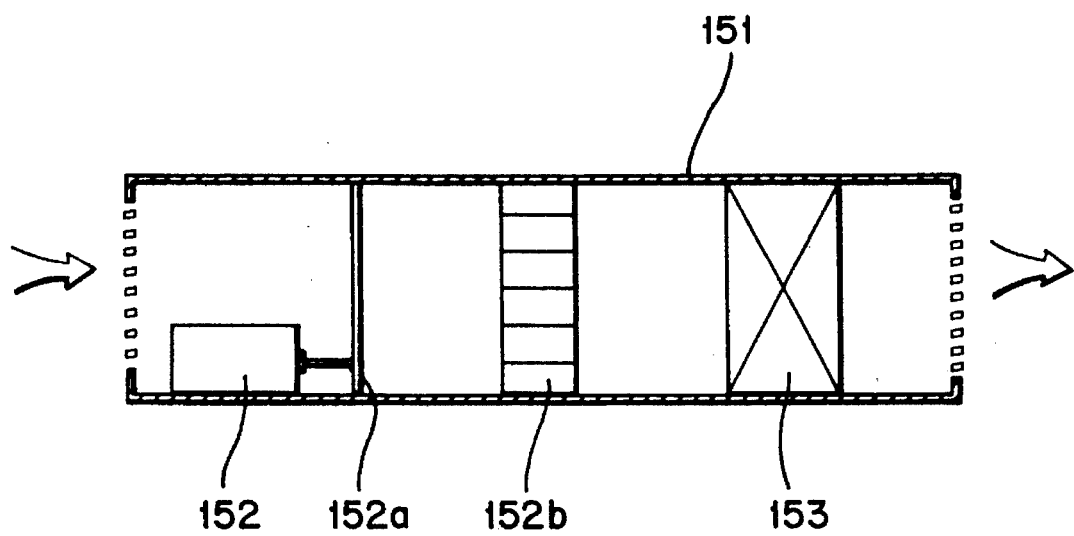
FIG. 2 is a cross-sectional view illustrating a sterilizing/deodorizing apparatus of the prior art; and, FIG. 3 is a cross-sectional view illustrating a multi-function apparatus according to the invention.

According to the invention, a multi-function apparatus is adapted to a refrigerator shown in FIG. 1 and mounted in the same position as that of a conventional sterilizing/deodorizing apparatus 5 without consuming additional storage space.

Figure 3:
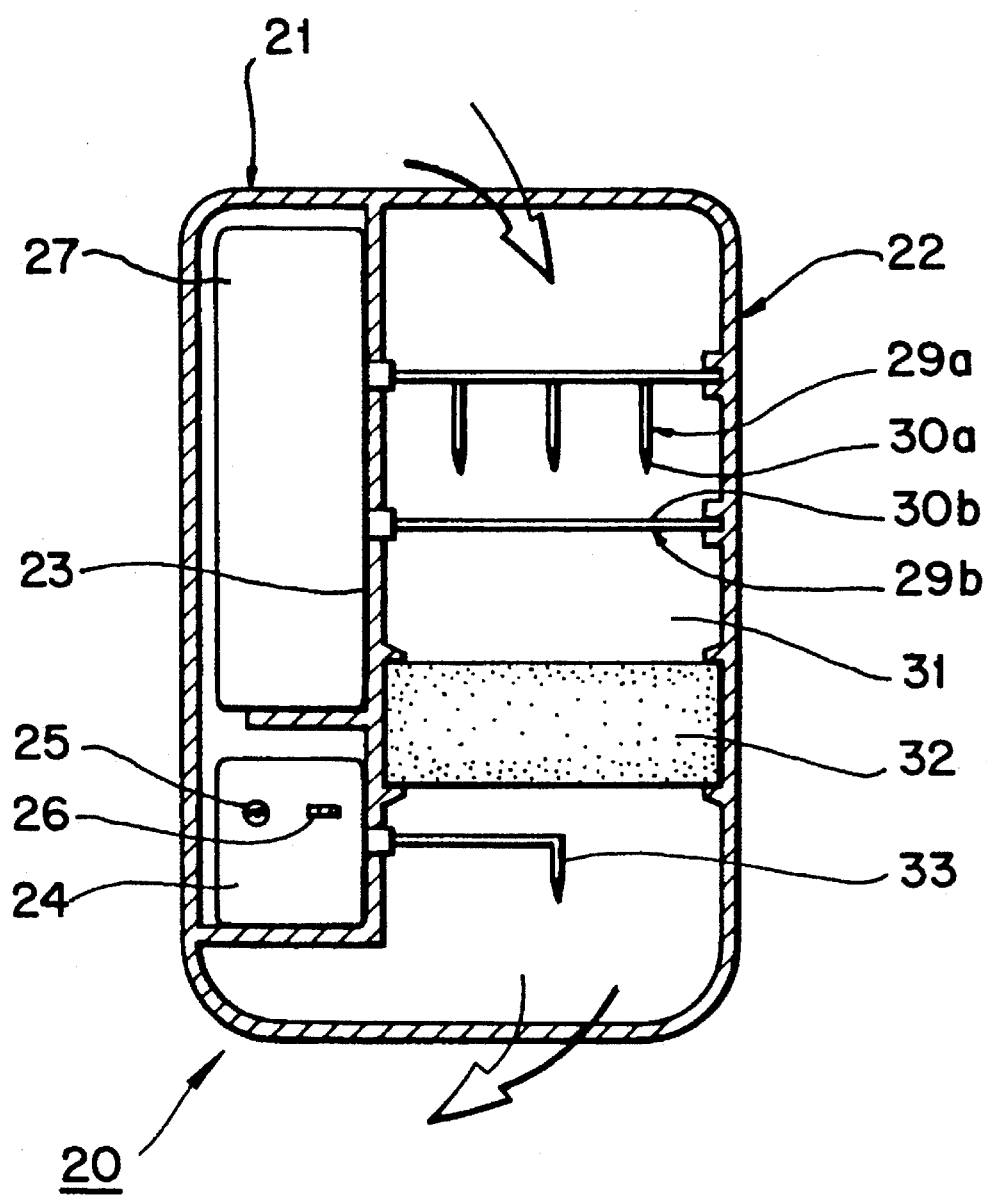

The multi-function apparatus 20 comprises a power source portion 21 and a multi-function additional portion 22 separated by a partition wall 23 as shown in FIG. 3.

The power source portion 21 is a system control circuit which includes a printed circuit board 24 provided with an indicating light 25 which enables users to monitor the system operation and an on/off switch 26 for controlling the power source and a high voltage generator 27 for generating a plurality of positive or negative high voltages.

The multi-function additional portion 22 is provided with a pointed electrode structure 29a and a strip shaped electrode structure 29b, arranged in sequence at a predetermined interval from the upper air inlet portion to perform the corona discharge, and to which the negative and positive high voltages are applied. Since electrode structures are well known in the prior art, a detailed explanation is omitted here. But note that in the pointed electrode structure 29a, a plurality of pointed electrodes are aligned at predetermined intervals.

An area identified as an ozone reacting layer 31 is formed in a predetermined space below the electrode structures, in which ozone generated by the corona discharge of the electrode structures 29a and 29b sterilizes floating bacteria and deodorizes the odor from foodstuffs.

The ozone resolving portion 32 comprises an ozone resolving catalyst layer mounted directly below the ozone reacting layer 31.

The ionizing electrode 33 is located below the lower portion of the ozone resolving portion 32 with its pointed end curved downward. Positive or negative high voltage is applied to the ionizing electrode 33.

According to the configuration of the invention described above, in a refrigerator where foodstuffs are stored in selected compartments, when the refrigerating. cycle begins, a multi-function apparatus 20 is turned on and a high voltage generator 27 is supplied by to the power source in order to generate a plurality of high D.C. positive or negative voltages, which are selectively transmitted to the pointed electrode structure 29a and the strip-shaped electrode structure 29b to create the corona discharge. The corona discharge ionizes the air introduced around the pointed electrodes 30a and moves the air toward the surface 30b of the strip-shaped electrode structure 29b to form ion circulation.

In other words, the corona discharge between the electrode structures 29a and 29b ionizes the oxygen in air ($O_2 \rightarrow O^- + O^-$). The ionized oxygen atom ($O^-$) is combined with an oxygen ($O_2$) to form ozone ($O_3$). The ozone ($O_3$) is unstable enough to be reduced again. The ozone-containing air has a strong oxidizing effect which sterilizes floating bacteria and dissolves odors in the air introduced into the multi-function additional portion, thereby purifying the air in the refrigerator's compartments.

Also, the air purification is performed in the ozone reacting layer 31 and the ozone solving portion 32, in which the ozone solving portion 32 forces the ozone therein to be reduced to oxygen, thereby preventing the ozone from being emitted outside the housing. The purified air passing through the ozone solving portion 32 is ionized positively or negatively by the ionizing electrode 33, and the air containing positive or negative ions is discharged from the housing in order to maintain the freshness of the foodstuffs for an extended period of time. In particular, the ionizing electrode 33 is provided with a pointed end which is curved downward to conform with the direction from which the ion circulation is introduced into the housing, thereby improving the positive or negative ionization of the purified air.

According to the invention, a multi-function apparatus comprises an ozone generating portion for generating ozone and an ionizing electrode for generating positive or negative ions, which are both supplied by means of a high voltage generator, thereby sterilizing/deodorizing floating bacteria and odors in the refrigerator's compartment, preserving the freshness of foodstuffs for an extended period of time, and avoiding the need to consume additional space in the storage compartments.

What is claimed is:

1. A multi-function apparatus for use in a refrigerator comprising:

a housing;

a power source portion disposed in said housing for rectifying output of a power source and for generating a plurality of voltages; and a multi-function additional means disposed in said housing supplied with said voltages for generating corona discharge to perform sterilizing/deodorizing functions for purifying air in storage compartments of a refrigerator and for generating ions in the purified air;

said multi-function additional means comprising:

a plurality of pointed electrodes and a strip shaped electrode facing said plurality of pointed electrodes supplied by the voltages to generate corona discharge for ionizing air passing introduced around the plurality of pointed electrodes;

an ozone solving portion disposed on a side of said strip shaped electrode opposite from said plurality of pointed electrodes for preventing emission of ozone outside the housing by reducing the ozone to oxygen thus providing purified air; and an ionizing electrode means disposed downstream from said ozone solving portion for generating said ions in the purified air which passes through said ionizing electrode means, said ionizing electrode means having a pointed end which is curved downward along the direction the purified air passes through said ionizing electrode means.

2. The multi-function apparatus as claimed in claim 1, wherein said power source portion includes a printed circuit board, which operates as a circuit for controlling the multi-function apparatus and which rectifies output of the power source, and a high voltage generating portion for generating a plurality of positive or negative voltages.

3. The multi-function apparatus as claimed in claim 1, wherein said power source portion comprises means for generating a plurality of positive or negative voltages.

4. The multi-function apparatus as claimed in claim 1, wherein the multi-function additional means comprises means for generating positive or negative ions in the purified air.

* * * * *